United States Patent [19]

Cottenceau et al.

[11] Patent Number: 5,344,427
[45] Date of Patent: Sep. 6, 1994

[54] FILTER WITH TRIANGULAR FINGERS

[75] Inventors: Jean-Philippe Cottenceau, Antony; Gérard Chevillon, Montrouge, both of France

[73] Assignee: Celsa L.G. (Societe Anonyme), Chasseneuil, France

[21] Appl. No.: 90,959

[22] Filed: Jul. 13, 1993

[30] Foreign Application Priority Data

Aug. 7, 1992 [FR] France ................................ 92 09845

[51] Int. Cl.$^5$ ............................................... A61F 2/02
[52] U.S. Cl. ................................................... 606/200
[58] Field of Search ................. 606/191, 198, 199, 200

[56] References Cited

U.S. PATENT DOCUMENTS

| | | |
|---|---|---|
| 4,494,531 | 1/1985 | Gianturco . |
| 4,643,184 | 2/1987 | Mobin-Uddin ...................... 606/198 |
| 4,655,771 | 4/1987 | Wallsten ................................ 623/1 |
| 4,688,553 | 8/1987 | Metals . |
| 4,727,873 | 3/1988 | Mobin-Uddin ...................... 606/200 |
| 4,954,126 | 9/1990 | Wallstén .............................. 606/36 |
| 5,035,706 | 7/1991 | Giantureo et al. .................. 606/198 |
| 5,059,205 | 10/1991 | El-Nounou et al. ................. 606/200 |
| 5,104,399 | 4/1992 | Lazarus ................................ 623/1 |
| 5,133,733 | 7/1992 | Rasmussen et al. ................ 606/200 |

FOREIGN PATENT DOCUMENTS 3417738 11/1985 Fed. Rep. of Germany .
4030998 4/1991 Fed. Rep. of Germany .

*Primary Examiner*—Tamara L. Graysay
*Attorney, Agent, or Firm*—Rothwell, Figg, Ernst & Kurz

[57] ABSTRACT

The filter includes a plurality of resilient fingers (2) which can be unfolded and are provided at their free ends with centering and bearing runners (5) for engaging an interior wall of a blood vessel. In accordance with a preferred embodiment of the invention, the fingers and the runners consist of flexible wires that are assembled with groups of two adjacent fingers being joined by a wire part folded in the shape of a hairpin.

7 Claims, 5 Drawing Sheets

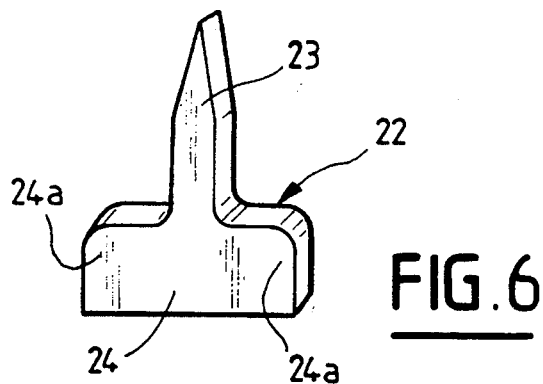
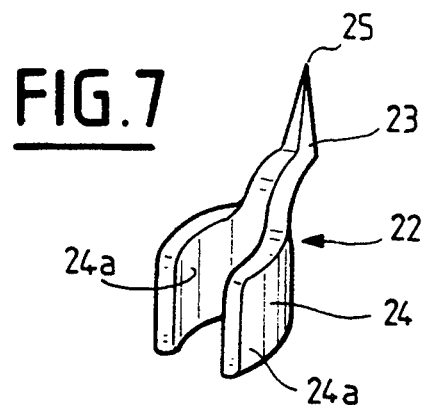
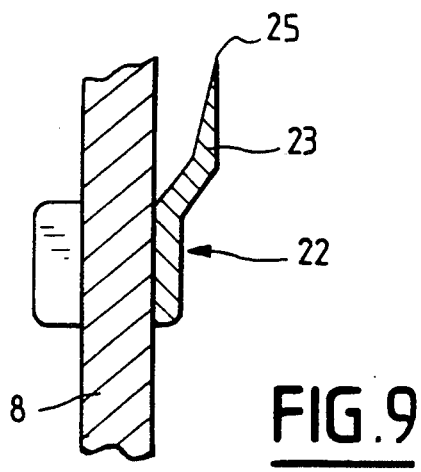
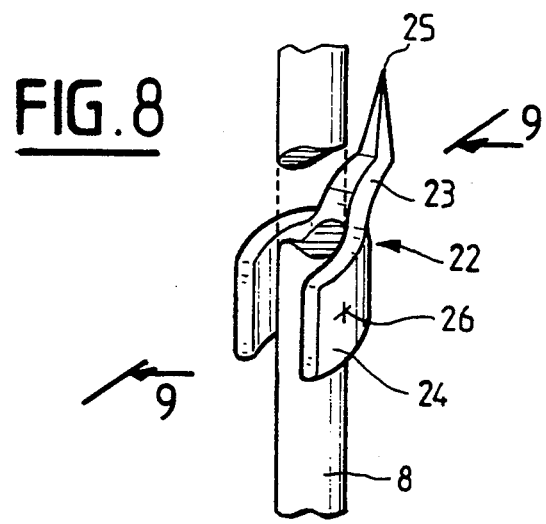
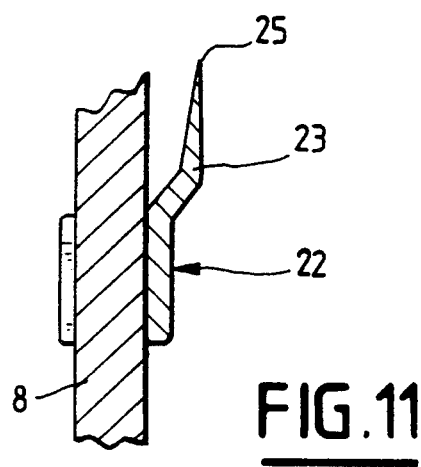
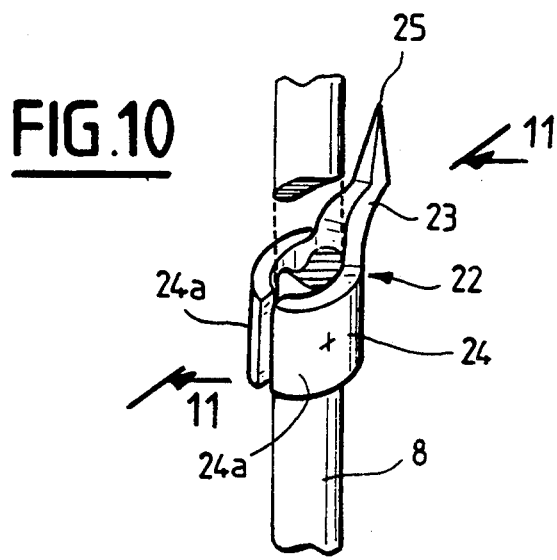

FILTER WITH TRIANGULAR FINGERS

BACKGROUND OF THE INVENTION

The invention relates to a filter to be placed in the blood system and in particular in the course of a vein for retaining blood clots.

Filters of this type are described for example in U.S. Pat. No. 4,088,553.

Generally, these filters are in the form of a small frustoconical basket which attaches to the interior of a vein downstream of the path which is desired to be filtered; this is generally the vena cava arriving at the heart. It is thus possible to stop any blood clots which can form and, in particular causes embolisms, before such clots enter the heart.

Usually these filters are of two main types.

The first type noted is filters produced from metal wires assembled together by welding or crimping. These filters are small and flexible. Once bent, they are not bulky and are well-suited to insertion by routes which are difficult and have pronounced anatomical curvatures.

Furthermore, there are noted filters produced from plates generally enabling the filtering portion to be produced in one part which is cut out and shaped. These filters have a large bearing surface in contact with the vein, thus reducing trauma and eliminating the risks of perforation.

However, these two types of filters have various disadvantages.

With respect to the filters produced with wires, the flexibility of the wires causes two considerable problems:

firstly it prevents consistent bearing forces from being applied to the vein wall, the filter is thus not held well and can migrate;

secondly, the wire is small, and the bearing surface in contact with the vein is then restricted which can give rise to trauma and perforations.

Furthermore, there is a risk of the wires becoming tangled at the moment when the device is fitted, thus reducing the filtering capacity of the filters.

The filters produced from plates have a high degree of rigidity in their confined fitting position which renders them awkward to fit via routes which are initially sinuous. These filters are considerably bulky owing to the fact that the surfaces thereof which do not permit very fine insertion devices to be used increase trauma at the point of puncture.

Furthermore, filters formed from a conical portion provided with filtering components are generally difficult to position correctly. Generally, in order to introduce a filter of this type into the blood vessel, it is pushed there by means of a tube known as a catheter which passes through the said vessel and of which the diameter is less than that of the latter. When the filter arrives at the end of the insertion tube, it is released into the vessel and the expansion of its fingers, which are frequently provided with hooks, anchors it in place.

In practice a "release" of this type is very awkward to control. In a certain number of cases it has ensued that the basket-type filter in fact occupies a position other than the most favourable position inside the vessel, i.e., a position in which the axis of the filter is substantially parallel with the axis of the vessel.

SUMMARY OF THE INVENTION

The object of the present invention is to overcome these disadvantages by proposing a filter with a certain degree of flexibility in order to facilitate positioning, and with a degree of rigidity and axial stability which are sufficient to ensure that it holds well in the vein and provides high quality filtration.

The filter according to the invention is of the general type consisting of a plurality of resilient fingers which can be unfolded substantially into a generally conical shape emerging from a head, each finger being provided at its free end with a centering and bearing runner directed in the unfolded position such that it is substantially parallel to the substantially cylindrical wall produced by a generating line parallel with the axis of the said conical shape and describing as a generating line the opening parameter of the said conical shape in a normal position of use. More particularly, the filter is characterised in that the said fingers, as well as the runners, consist of flexible wires and are combined in groups of two adjacent fingers by a piece of wire folded in the manner of a hairpin, which wire forms the said runners provided at the corresponding ends of the fingers.

In this way, when the filter is positioned in the vein, it has a broad supporting area which decreases trauma owing to the contact pressure on the vein walls; moreover, the centering and bearing runners are held firmly from the outset against the vein walls, forcing the filter to adopt a position such that its axis merges substantially with the axis of the vein.

The particular wire structure enables the fingers and their runners to be deformed in several directions, which enables the fingers to be grouped in a small space and facilitates fitting by virtue of fine insertion devices. Furthermore, combining the fingers in pairs prevents their becoming tangled.

In accordance with one feature of a preferred embodiment of the invention, the wire portions folded in the manner of a hairpin turn substantially backwards whilst being directed towards the head of the cone.

In accordance with a further feature of the invention, the fingers combined in groups of two adjacent fingers consist of a single wire folded on itself in the shape of a clip and held locally at the head.

In accordance with a variant of the invention, the wire portions folded into the shape of a hairpin define substantially triangular areas. This particular shape or "triangulation" of the wires enables the two ends of each wire to be moved together easily. In the folded position, the filter then occupies a small amount of space, with the two ends of the wires extending substantially adjacent one another, and along each other, the assembly of the wire bundle retaining all its flexibility without the risk of becoming tangled when the filter is released in the vein.

In accordance with a further feature of the invention, at their end opposite that which is joined to the runners, the flexible wires constituting the fingers are secured in a solid head of a generally ogival shape and having preshaped holes.

The invention further relates to means for attaching the filter to the vein, for example, anchorage hooks.

BRIEF DESCRIPTION OF THE DRAWINGS

A more detailed description of the invention will now be given with reference to the accompanying drawings provided solely by way of non-limiting example and in which:

FIGS. 6 and 7 show two successive stages of the formation of a hook;

FIG. 8 shows the securing of a hook on the wire, the base of the hook being flattened about the wire;

FIG. 9 shows in section the securing of the hook substantially along the section line 9—9 in FIG. 8;

FIG. 10 shows a variant of the securing of the hook, the base of the hook being folded about the wire;

FIG. 11 shows in section along the section line 11—11 in FIG. 10 the variant of the securing of the hook.

DETAILED DESCRIPTION OF THE DRAWINGS

Figure 1:
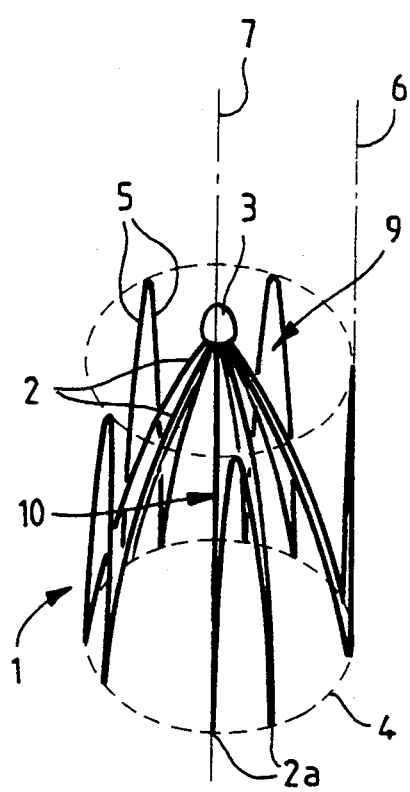
FIG. 1 shows schematically in perspective a filter in accordance with the invention in its unfolded state.

With reference firstly to FIG. 1, there is thus illustrated a filter 1 in the unfolded position consisting of fingers 2, of which there are ten for example, which emerge from a head 3 and which can be unfolded substantially in a generally conical shape of which the opening is marked in dashed lines at 4. Each finger is provided at its free end with a centering and bearing runner 5 which turns substantially behind the head 3; that is, this runner 5 is directed from the end 2a of the fingers towards the closure side of the cone forming the filter. More precisely, if we designate as 6 the cylinder generated by a generating line that is parallel with the axis 7 of the conical shape formed by the filter 1 and moved such that it describes the line 4, the runners 5 are directed such that they are substantially parallel with the wall of the cylinder 6.

In accordance with the invention, the filter fingers consist of flexible wires 8. They may in particular consist of metal wires, for example of a suitable grade of stainless steel, such as that known as AFNOR K 13C20 N16 Fe15 for example, known in particular by and sold under the registered trade mark of "PHYNOX"; the diameter of the wires may be between 2 and 4 tenths of a millimetre for example 3 or 3.5 tenths of a millimetre.

Figure 3:
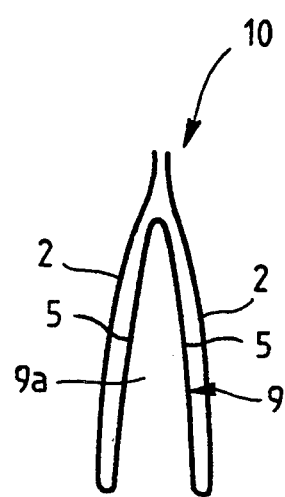
FIG. 3 is a detailed view of two adjacent fingers Joined to one another.

These fingers are combined in groups of two adjacent fingers by a wire part which is folded in the manner of a hairpin 9 and forms said runners. As a result, the fingers are in the general shape of a clip 10, as illustrated in FIG. 3 below. Advantageously, the filter preferably comprises at least six of the above fingers connected to three wire portions folded in the manner of a pin and distributed in an angular manner so as to ensure that the filter has good axial stability.

A filter according to the invention is positioned in a blood vessel according to the conventional process which is facilitated by the flexibility of the filter.

Figure 2:
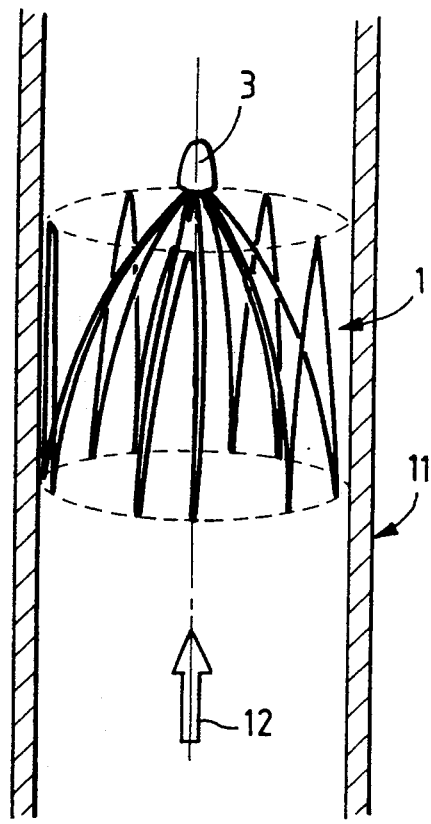
FIG. 2 shows schematically the filter implanted in a vessel.

FIG. 2 illustrates a filter 1 implanted in the unfolded position inside a vessel 11 such that it can intercept any clots circulating therein, the direction of the blood flow being marked by the arrow 12. The runners 5 are held firmly against the inner wall of the vein thus enabling the filter to centre itself in the vessel.

FIG. 3 shows a detailed view of a clip 10 consisting of two adjacent fingers 2 joined by a wire portion folded in the form of a pin 9. Advantageously, this pin-like wire portion delimits a substantially triangular area 9a such that greater stability of the implanted filter in ensured.

Figure 5:
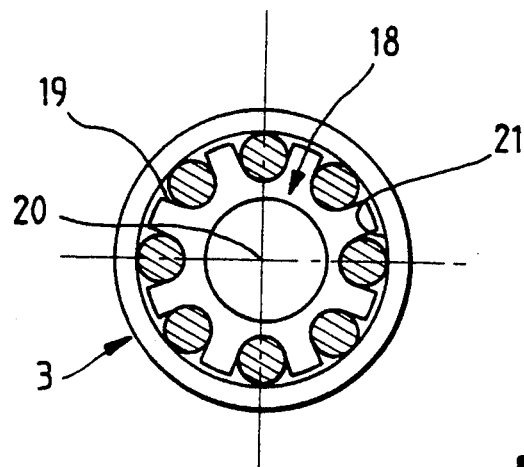
FIG. 5 shows a bottom view of FIG. 4, substantially along the section line 5—5 in FIG. 4.
Figure 4:
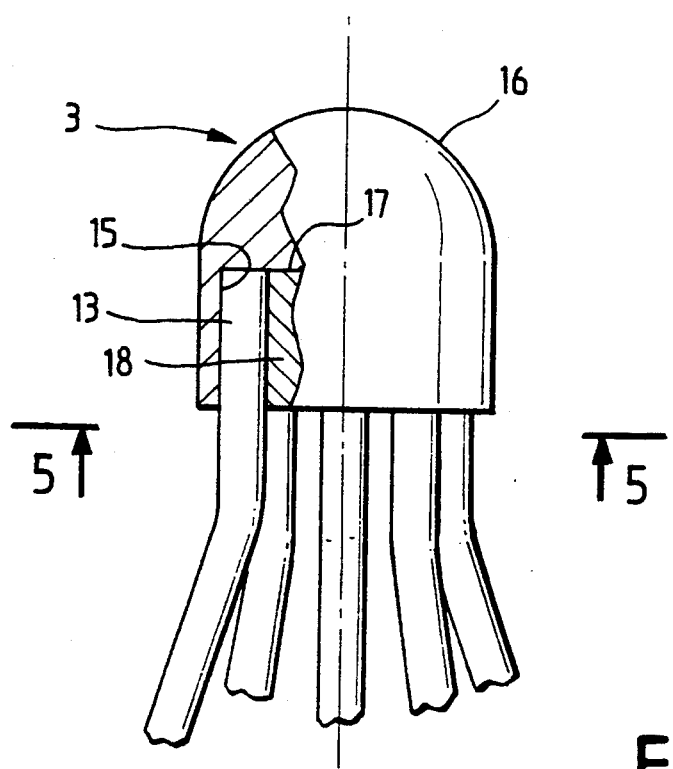
FIG. 4 shows the securing of the wires in a head, the lefthand third of the Figure being in section.

FIGS. 4 and 5 show the connection of the ends of the wires at the location of the head 3.

In accordance with FIG. 4, the ends 13 of the wires forming the fingers opposite those joined to the runners are secured in a head. The ends of the wires are inserted in an equivalent number of holes 15 preformed in the head. Advantageously, the head with a substantially ogival external surface 16 comprises a cylindrical bore 17 at its base end. The wires are secured in the head by virtue of a generally cylindrical part 18 of which the diameter and height are substantially equal to those of the bore and which have recesses 19 parallel with the axis of rotation 20 of the portion and opening onto the outer surface of the portion. These recesses 19 are distributed in an angular manner and the ends of the wire which are located therein are then secured by the inner wall 21 of the head as shown in FIG. 5.

The so-called definitive filters which are inserted when there is a constant risk of the passage of clots and which thus remain in place for the duration of the patient's life are provided with attachment means in order to prevent any migration of the filter in the vessel.

The filters according to the invention are provided with attachment means of this type which are to penetrate the wall of the vessel slightly. In effect, at least some of their runners are provided with anchorage hooks.

With reference to FIGS. 6 and 7, the constitution and manufacturing process of these anchorage hooks will now be described.

The starting point is a thin plate made of metal for example from which the blank of a hook 22 is cut out, as shown in FIG. 6, substantially in the shape of a T of which the staff is a tapered part 23.

The said blank formed in this manner is subjected to a shaping operation as illustrated in FIG. 7. Firstly, the tapered portion is made substantially V-shaped as a result of being moved away from the plane of the blank. The bar 24 of the T-shape is likewise shaped by the folding of its two arms 24a until they are substantially parallel. Subsequently, the said tapered portion 23 is sharpened such that its end forms a point 25.

Reference will now be made to FIGS. 8 to 11 for the description of the positioning of the hook on an arm of the wire.

FIGS. 8 and 9 show a first technique for securing hooks on the wires. The hook 22 placed on the wire 8 is secured as a result of the arms 24a of the bar 24 being flattened about the wire at points 26, as shown in FIG. 8.

As shown in FIG. 9, which illustrates a view in section of FIG. 8, the arms 24a remain free and parallel.

FIGS. 10 and 11 show a second possible technique for securing the hooks. In accordance with FIG. 10, the hook 22 is placed on the wire 8, the two arms 24a then being folded about the said wire.

FIG. 11 shows a view in section of FIG. 10 illustrating the folding of the arms 24a of which the ends are close to each other.

Figure 12:
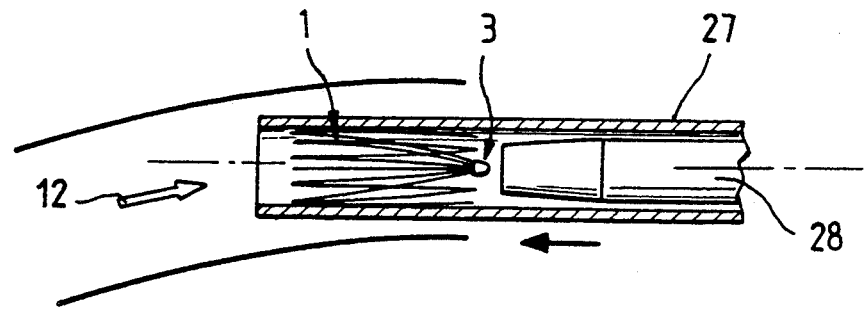
FIGS. 12, 13, 14 shows three successive stages for positioning the filter according to the invention in a vessel.
Figure 13:
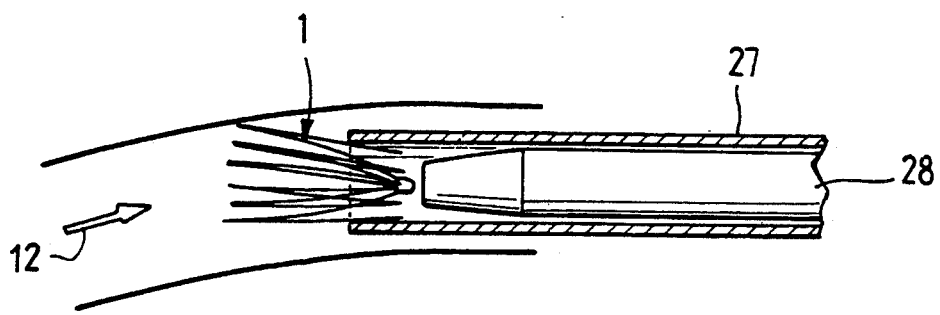
Figure 14:
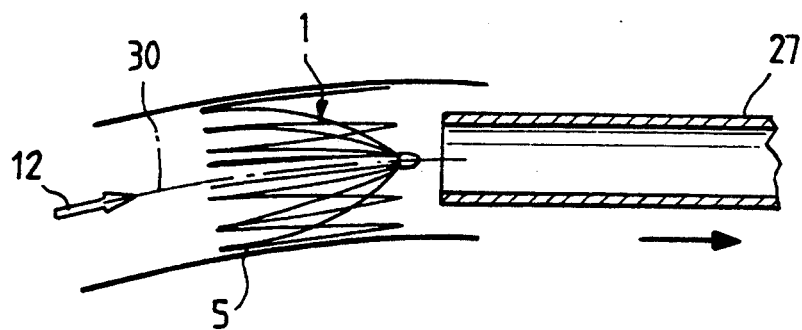

FIGS. 12, 13, 14 illustrate schematically a method of inserting the filter according to the invention in a vessel.

The filter is positioned through an insertion tube 27 which may be, e.g., a tube generally known in the art and sold under the trademark as a "DESILET".

In FIG. 12, the filter 1 is pushed inside the tube 27 by means of a pusher 28. It will be noted that the filter, in the folded position, is positioned such that its head 3 emerges last, the tube 27 having been introduced against the flow of blood indicated by the arrow marked 12.

In FIG. 13, the filter 1 appears emerging from the tube and already having a substantially conical shape.

FIG. 14 shows the filter 1 a moment later. The fingers are completed unfolded and their runners 5 defines a substantially cylindrical envelope which is almost coaxial with the axis 30 of the vessel and bears against its walls ensuring that the filter centres itself in the vein.

The tube 27 can then be withdrawn via its access route.

The positioning described above corresponds to the fitting of a filter by the jugular route. If it is fitted via the femoral route, the filter is released into the vein in the opposite direction, head first, where once again the triangular fingers constituting the filter ensure that it is centred.

It is evident that the present invention is only described purely by way of non-limiting example and that any useful modification can be made thereto without departing from its scope as defined by the following claims. Thus, according to a variant, the filters described can be used perfectly as temporary filters and in this case they are not provided with anchorage hooks.

Figure 15:
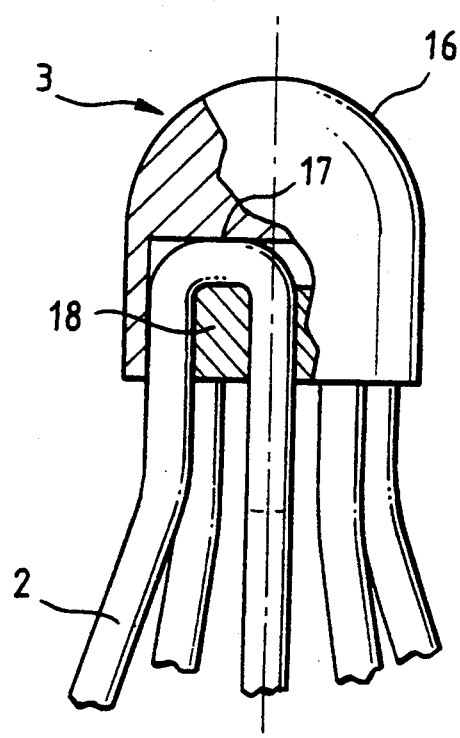
FIG. 15 is a partially sectioned view of an additional embodiment of the present invention.

In accordance with a further embodiment shown in FIG. 15, the said clips can all be formed from a single flexible wire suitably shaped and held substantially at points on the head.

We claim:

1. A filter to be placed within a blood vessel to retain blood clots, said filter comprising:

a head;
   a plurality of clips, each of said clips including a pair of first and second adjacent resilient fingers, each finger having a first end and a second end, and a hairpin-shaped piece of wire having a first end and a second end;
   said second ends of said first and second fingers being connected respectively to said first end and said second end of said hairpin-shaped piece of wire;
   said first and second fingers of said plurality of clips being arranged, in the region of the first ends of said first and second fingers, so as to emerge from said head in a substantially conical shape when said filter is inserted within said vessel;
   said hairpin-shaped piece of wire extending substantially parallel with a wall of said vessel when said filter is positioned within the vessel, and being directed substantially backwards toward said head; and
   wherein said pair of fingers and said hairpin-shaped piece of wire of each of said plurality of clips are formed from a single folded wire, said wire being held locally at said head.

2. A filter according to claim 1, wherein said plurality of clips are all made of a single flexible wire suitably shaped and held substantially locally at said head.

3. A filter according to claim 1, wherein each of said hairpin-shaped pieces of wire defines a substantially triangular area.

4. A filter according to claim 1, comprising at least three of said clips, said clips being angularly distributed about a longitudinal axis of said filter.

5. A filter according to claim 1, wherein the first ends of said first and second fingers are disposed in holes provided in said head.

6. A filter according to claim 1, wherein at least some of said hairpin-shaped pieces of wire are provided with anchorage hooks.

7. A filter according to claim 6, wherein each of said anchorage hooks is metallic and includes two arms which are secured on a corresponding hairpin-shaped piece of wire.

* * * * *